United States Patent
Rogge et al.

(10) Patent No.: US 11,249,090 B2
(45) Date of Patent: Feb. 15, 2022

(54) IMMUNOLOGICAL SIGNATURES AND PARAMETERS PREDICTING THERAPEUTIC RESPONSES TO ANTI-TNF THERAPY

(71) Applicants: INSTITUT PASTEUR, Paris (FR); ASSISTANCE PUBLIQUE-HOPITAUX DE PARIS, Paris (FR); UNIVERSITE PARIS DESCARTES, Paris (FR)

(72) Inventors: Lars Rogge, Issy les Moulineaux (FR); Silvia Menegatti, Paris (FR); Maxime Dougados, Paris (FR); Elisabetta Bianchi, Paris (FR)

(73) Assignees: INSTITUT PASTEUR, Paris (FR); ASSISTANCE PUBLIQUE—HOPITAUX DE PARIS, Paris (FR); UNIVERSITE DE PARIS, Paris (FR)

(*) Notice: Subject to any disclaimer, the term of this patent is extended or adjusted under 35 U.S.C. 154(b) by 88 days.

(21) Appl. No.: 15/761,238

(22) PCT Filed: Sep. 27, 2016

(86) PCT No.: PCT/EP2016/072969
§ 371 (c)(1),
(2) Date: Mar. 19, 2018

(87) PCT Pub. No.: WO2017/055268
PCT Pub. Date: Apr. 6, 2017

(65) Prior Publication Data
US 2018/0267058 A1    Sep. 20, 2018

(30) Foreign Application Priority Data
Sep. 29, 2015   (EP) .................................... 15306536

(51) Int. Cl.
| | | |
|---|---|---|
| *G01N 33/68* | (2006.01) | |
| *C12Q 1/6883* | (2018.01) | |
| *A61P 19/02* | (2006.01) | |
| *A61K 39/02* | (2006.01) | |
| *A61K 39/145* | (2006.01) | |
| *A61K 39/00* | (2006.01) | |

(52) U.S. Cl.
CPC ....... *G01N 33/6863* (2013.01); *A61K 39/105* (2013.01); *A61K 39/145* (2013.01); *A61P 19/02* (2018.01); *C12Q 1/6883* (2013.01); *A61K 2039/521* (2013.01); *C12Q 2600/106* (2013.01); *C12Q 2600/158* (2013.01); *G01N 2333/52* (2013.01); *G01N 2800/102* (2013.01); *G01N 2800/52* (2013.01); *G01N 2800/56* (2013.01); *G01N 2800/60* (2013.01)

(58) Field of Classification Search
None
See application file for complete search history.

(56) References Cited

U.S. PATENT DOCUMENTS

2012/0088678 A1* 4/2012 Albani ................. C12Q 1/6883
506/7

FOREIGN PATENT DOCUMENTS

| CN | 102507883 A | 6/2012 |
|---|---|---|
| WO | WO 2008/150491 A2 | 12/2008 |
| WO | WO 2010/077722 A1 | 7/2010 |

OTHER PUBLICATIONS

Arends et al. The Journal of Rheumatology 2011; 38:8. (Year: 2011).*
Arend, William, Arthritis Care and Search vol. 45 No. 1, pp. 100-106 2001. (Year: 2001).*
Sekiguchi Net Al: "Messenger ribonucleic acid expression profile in peripheral blood cells from RA patients following treatment with an anti-TNF-alpha monoclonal antibody, infliximab." Rheumatology, Oxford University Press, London, GB, vol. 47, No. 6, Apr. 3, 2008 (Apr. 3, 2008), pp. 780-788, XP002562468, ISSN: 1462-0324, DOI: 10.1093/RHEUMATOLOGY/KEN083.
Stuhlmuller B Ei Al: "CD11c as a transcriptional biomarker to predict response to anti-TNF monotherapy with adalimumab in patients with rheumatoid arthritis", Clinical Pharmacology and Therapeutics, Nature Publishing Group, US, vol. 87, No. 3. Dec. 29, 2009 (Dec. 29, 2009), pp. 311-321, XP009136707,ISSN: 0009-9236.
Lequerre Thierry et al: "Gene profiling in white blood cells predicts infliximab responsiveness in rheumatoid arthritis", Arthritis Research and Therapy, Biomed Central, London, GB, vol. 8, No. 4, Jul. 3, 2006 (Jul. 3, 2006), p. R105, XP021020585, ISSN: 1478-6354, DOI: 10.1186/AR1924.
International Search Report for PCT/EP2016/072969, dated Dec. 6, 2016.

* cited by examiner

*Primary Examiner* — Jana A Hines
*Assistant Examiner* — Khatol S Shahnan Shah
(74) *Attorney, Agent, or Firm* — Arrigo, Lee, Guttman & Mouta-Bellum LLP (57) ABSTRACT

The invention relates to a method of predicting therapeutic responses to TNF blockers before anti-TNF therapy comprising analyzing immune parameters to selected stimuli in patients before therapy and its use for anti-TNF therapy. The invention relates also to a method of determining a predictive biomarker of response to anti-TNF therapy and to the use of the predictive biomarker obtained by the method.

22 Claims, 5 Drawing Sheets
Specification includes a Sequence Listing.

SEQUENCE LISTING

```
<160> NUMBER OF SEQ ID NOS: 1

<210> SEQ ID NO 1
<211> LENGTH: 20
<212> TYPE: DNA
<213> ORGANISM: artificial sequence
<220> FEATURE:
<223> OTHER INFORMATION: synthetic

<400> SEQUENCE: 1
gggggacgat cgtcgggggg                                              20
```

IMMUNOLOGICAL SIGNATURES AND PARAMETERS PREDICTING THERAPEUTIC RESPONSES TO ANTI-TNF THERAPY

The present invention relates to a method of predicting therapeutic responses to TNF blockers before anti-TNF therapy comprising analyzing immune parameters to selected stimuli in patients before therapy and its use for anti-TNF therapy. The invention relates also to a method of determining a predictive biomarker of response to anti-TNF therapy and to the use of the predictive biomarker obtained by the method.

Chronic inflammatory diseases cause significant morbidity and are a considerable burden for the patients in terms of pain, impaired function and diminished quality of life, as well as for society, because of the associated high healthcare costs, and loss of productivity. The spondyloarthritis (SpA) group of diseases are among the most common inflammatory rheumatic diseases, with a prevalence estimated to be in the range of 0.5-1.5% of the population (Smith and Colbert, 2014), and consist of several disorders: psoriatic arthritis, reactive arthritis, arthritis related to inflammatory bowel disease, a subgroup of juvenile chronic arthritis and ankylosing spondylitis. An experimental argument in favor of grouping these entities in a single family is the fact that HLA-B27 transgenic rats, the animal model for SpA, develop the different clinical manifestations observed in humans with SpA (Jenkinson et al., 1994). The clinical argument in favor of this concept is the fact that such disorders may occur simultaneously or sequentially in a single patient or in a member of his/her family. The different clinical manifestations observed in SpA include spinal (axial) manifestations, peripheral arthritis, enthesitis and extra-articular features such as uveitis, psoriasis and inflammatory bowel disease (Baeten et al., 2013b; Dougados and Baeten, 2011). The axial symptoms are the most frequent and predominant at an early stage of the disease. SpA typically develops in young adults and has a dramatic impact on their quality of life, because of its disabling rheumatic manifestations, and the severe extra-articular manifestations that may develop in some patients (Dougados and Baeten, 2011). The prototypic SpA form, ankylosing spondylitis (AS), which affects 0.55% of populations of European ancestry (Braun et al., 2005; Rudwaleit et al., 2009; Rudwaleit et al., 2006), has a strong genetic component, with 80-90% of susceptibility attributable to genetic factors. The main genetic risk factor is the MHC class I molecule HLA-B27, carried by 80-90% of patients. However, the presence of HLA-B27 explains only 20-40% of the genetic risk of developing AS, suggesting an important role for additional genes in AS pathogenesis (International Genetics of Ankylosing Spondylitis et al., 2013; Robinson and Brown, 2014).

Our very limited understanding of the mechanisms involved in disease pathogenesis and in the responsiveness to treatment currently hinders the development of more specific and effective therapies.

The introduction of anti-TNF therapy has proven effective to reduce inflammation and clinical symptoms in several chronic inflammatory diseases, such as rheumatoid arthritis, Crohn's disease, ulcerative colitis, psoriasis, psoriatic arthritis and spondyloarthritis (SpA). However, TNF-blockers can be associated with serious side effects and are effective only in a subpopulation of patients.

TNF blockers are being used as second-line treatment in SpA since 15 years. They are administered to patients who do not respond to or do not tolerate non-steroidal anti-inflammatory drugs (NSAIDs). However, as for other chronic inflammatory diseases, 30-40% of SpA patients do not respond or respond inadequately to treatment with TNF blockers. Recent clinical trials have demonstrated that anti-IL-17A therapy is effective in SpA (Baeten et al., 2013a) and this new therapy will be introduced in the clinics in 2016. In addition to the standard first-line therapy with NSAIDs, there will therefore be two options for SpA patients who do not respond adequately to NSAIDs, i.e. TNF-blockers and anti-IL-17A therapy.

Despite intense efforts, it is currently not possible to predict responsiveness of patients to anti-TNF therapy. In clinical practice, non-responsive patients are being switched to another TNF blocker or other molecules until an effective therapeutic agent is identified. This procedure is expensive and may take a long time, during which the patient is not appropriately treated and is exposed to side effects without clinical benefit. Stratification of SpA patients to the most effective therapy is of key importance; both in terms of optimal clinical care and health care costs. To improve clinical outcome, there is a need for tools that allow prediction of treatment responses. Developing biomarkers that will help patients and physicians to choose the most effective therapy is an unmet medical need that needs to be urgently addressed.

WO 2014/198727 discloses a method of predicting a response to TNF blockers treatment in rheumatoid arthritis patients comprising detecting differential expression of a biomarker selected from the group consisting of: Complement component C7 precursor (CO7), Vitamin K-dependent protein S precursor (PROS), Protein S100A9, Ceruloplasmin precursor (CERU), Inter-alpha trypsin inhibitor heavy chain H1 precursor (ITIH1), Zinc-alpha-2-glycoprotein precursor (ZA2G), plasminogen precursor (PLMN), Inter-alpha trypsin inhibitor heavy chain H3 precursor (ITIH3), Complement C1r subcomponent precursor—IC1), Serotransferrin precursor (TRFE) and CPN2 (Carboxypeptidase N subunit 2 precursor (CPN2), in a blood sample obtained from the patient before starting anti-TNF therapy. The assay is performed directly on the sample, by measuring the amount of biomarker protein or mRNA present in the sample as obtained from the patient.

The inventors have taken a new approach to address this issue by investigating the effects of anti-TNF therapy on innate or adaptive immune responses to stimuli targeting different signaling pathways or mimicking infections in SpA patients. They have performed a pilot study with a cohort of SpA patients using whole-blood stimulation cultures ("TruCulture" assays; Duffy et al., 2014). The "TruCulture" assay is a highly standardized ex vivo assay that preserves physiological cellular interactions and allows for precise measurements of immune parameters, with and without stimulation. This assay is designed to capture immune cell activity without introducing sample collection and manipulation variables (transport of blood samples, Ficoll gradient, etc.). 28 different TruCulture assays targeting specific pathways (TLR agonists, TCR agonists, cytokines) or mimicking infections (heat killed *Staphylococcus aureus*/*Candida Albicans*, inactivated influenza virus, etc.) were established and validated on 1000 healthy donor. The study provided healthy donor reference values for cytokines and chemokines induced by these stimuli.

Using this assay system the inventors have investigated if they could detect changes in immune responses to 20 different stimuli in patients before and 3 months after initiation of anti-TNF therapy. In this pilot study, 11 patients were treated with Etanercept, and 1 patient with Adalimumab. They noted a highly significant reduction of the secretion of several pro-inflammatory cytokines and chemokines as well as of the matrix metalloproteinase MMP-9 in response to selected stimuli after treatment with TNF-blockers. In contrast, TNF blockers had only minor effects on cytokine/chemokine production in unstimulated cultures, indicating that the effects of anti-TNF therapy can be measured when immune cells are challenged, but not at steady state. These data suggest that there is a correlation between the responses of immune cells to specific stimuli and the therapeutic response to TNF-blockers.

Therefore, the inventors also asked whether there is a correlation between the responses of immune cells to specific stimuli and the clinical response to TNF-blockers. For this, they calculated the "Ankylosing Spondylitis Disease Activity Score" (ASDAS) before treatment and 3 months after initiation of anti-TNF therapy and determined the "Improvement Score" ($ASDAS_{before\ treatment}$-$ASDAS_{after\ treatment}$). They noted a trend towards the best improvement score for SpA patients who, before anti-TNF treatment, secreted the highest levels of inflammatory cytokines/chemokines in response to immune stimuli. Specifically, they found that following stimulation with *Helicobacter pylori* or Influenza virus, the levels of IL-1ra, MIP-1β and TNFα, as well as the levels of the matrix metalloproteinase MMP-9, were higher in whole-blood stimulation cultures from SpA patients who subsequently responded to anti-TNF therapy, than in non-responders or patients with a partial response. These results demonstrate that analyzing immune responses in patients before therapy is a novel and efficient strategy to develop biomarkers predicting therapeutic efficacy of TNF-blockers.

Therefore, the invention relates to a method of predicting a therapeutic response to anti-TNF therapy in a patient comprising the steps of:

a) obtaining a culture of immune cells from a biological sample collected from a patient prior to anti-TNF therapy, b) stimulating the culture with an agent that stimulates the innate or adaptive immune responses, c) measuring the expression level (mRNA or protein) of at least one biomarker induced by the stimulating agent at step b), and d) comparing the expression level measured at step c) with a reference value, wherein the detection of a higher or lower expression level of the biomarker between the stimulated culture and the reference value indicates that the patient will be a responder to anti-TNF therapy.

The invention provides biomarkers that can predict the therapeutic response to TNF-blockers before anti-TNF therapy. The biomarkers of the invention allow distinguishing between anti-TNF therapy responders and non-responders and subsequently sorting responder patients, before starting an anti-TNF therapy. The biomarker of the invention has thus the advantage of allowing the selection of the patients in which anti-TNF therapy will be efficient.

Predicting a status or event refers to making a finding that an individual has a significantly enhanced or reduced probability of having a given status or experienced an event.

TNF refers to tumor necrosis factor-alpha, TNF-alpha or TNF-α, a naturally occurring cell-signaling protein (cytokine), which plays a role in the regulation of immune cells and is involved in inflammation. It is mainly produced by macrophages but can also be produced by many other cell types (CD4+ lymphocytes, NK cells, neutrophils, mast cells, eosinophils and neurons).

anti-TNF therapy refers to the administration of a TNF blocker, blocking agent, inhibitor or antagonist. A TNF-blocker is a molecule such as a small molecule, protein or antibody that can significantly reduce TNF-alpha activity in a subject. Examples of TNF-blockers include anti-TNF-alpha antibodies such as for example infliximab, adalimumab, golimumab, certolizumab, CDP571, and the like, as well soluble TNF-receptor based proteins such as for example recombinant TNF-receptor IgG-Fc fusion protein (etanercept), pegylated soluble TNF type 1 receptor and the like.

Patient refers to a mammal, preferably a human suffering from a condition that can be treated by the administration of a TNF blocker.

Figure 3:
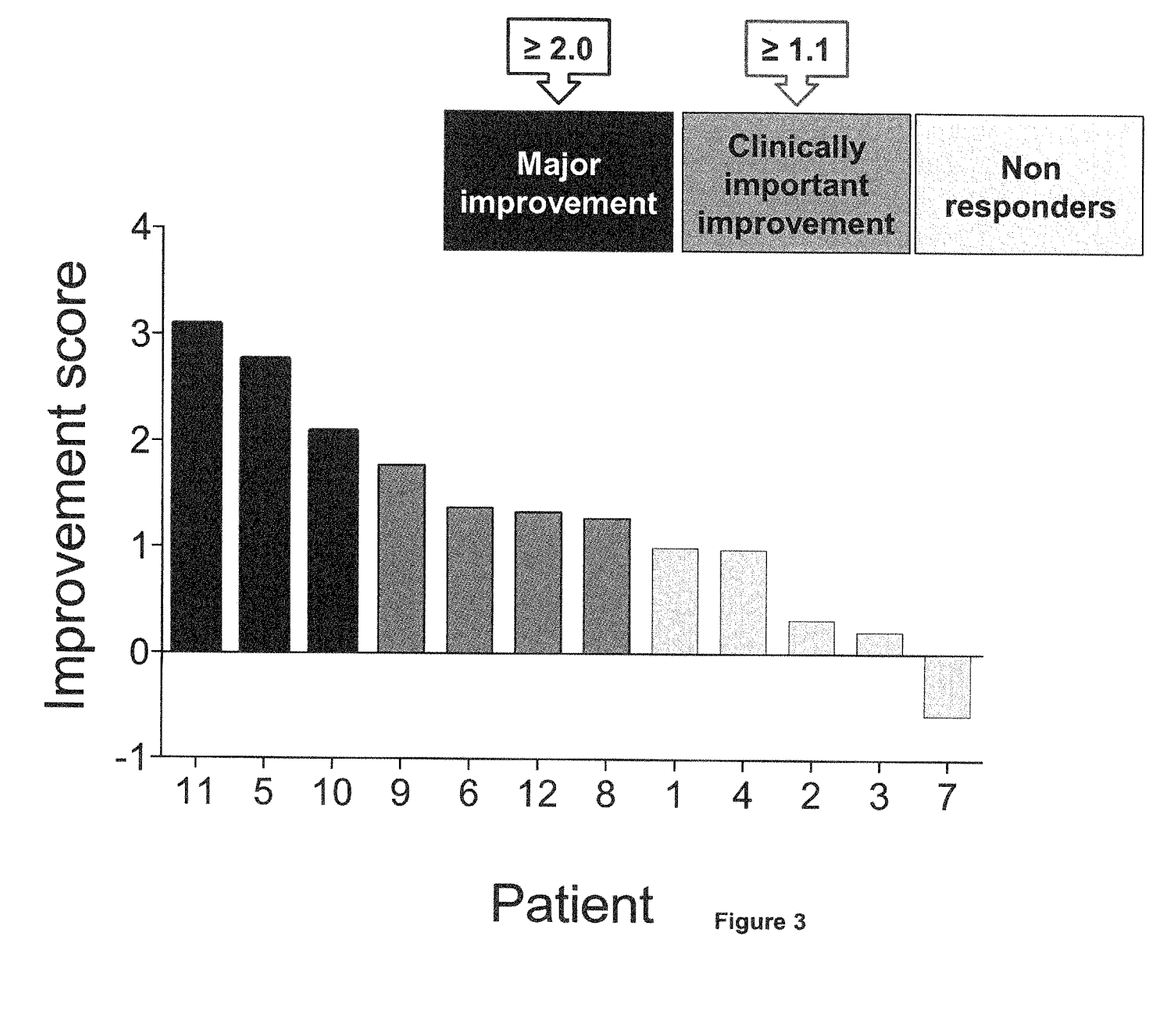
FIG. 3: Therapeutic responses to anti-TNF therapy. The "Ankylosing Spondylitis Disease Activity Score" (ASDAS) was calculated for each patient (Machado et al., 2011; Machado et al., 2015; van der Heijde et al., 2009) before treatment and 3 months after initiation of anti-TNF therapy. Shown is the "Improvement Score" ($ASDAS_{before\ treatment} - ASDAS_{after\ treatment}$) for each patient included in this study. Patients were grouped into non-responders (white bars), partial responders (grey bars), and responders (black bars) based on the improvement score.

Therapeutic response or response to anti-TNF treatment or therapy refers to a positive medical response to an anti-TNF treatment characterized by objective parameters or criteria such as objective clinical signs and patient self-reported parameters. The objective criteria for evaluating the response to anti-TNF treatment will vary from one disease to another and can be determined easily by one skilled in the art by using clinical scores. Response to treatment in spondyloarthritis patients uses the "Ankylosing Spondylitis Disease Activity Score" (ASDAS) (Machado et al., 2011; Machado et al., 2015; van der Heijde et al., 2009). An "Improvement Score" ($ASDAS_{before\ treatment}$-$ASDAS_{after\ treatment}$) can be determined. Patients are then grouped into Responders and Non-Responders or Responders, Partial responders and Non-Responders according to the improvement, as shown in the examples of the present application (FIG. 3).

Biological sample refers to a biological material comprising immune cells. The biological material that may be derived from any biological source is removed from the patient by standard methods which are well-known to a person having ordinary skill in the art.

Immune cells refers to cells of the immune system including in particular monocytes, macrophages, lymphocytes such as B-lymphocytes, T-lymphocytes, dendritic cells, NK cells, granulocytes and mixtures thereof.

Stimulated immune cells refers to immune cells stimulated with an agent that stimulates innate or adaptive immune responses.

Biomarker refers to a distinctive biological or biologically derived indicator of a process, event or condition.

Predictive biomarker refers to a biomarker that can be used in advance of therapy to estimate response and/or survival of a patient on a specific treatment.

Figure 5:
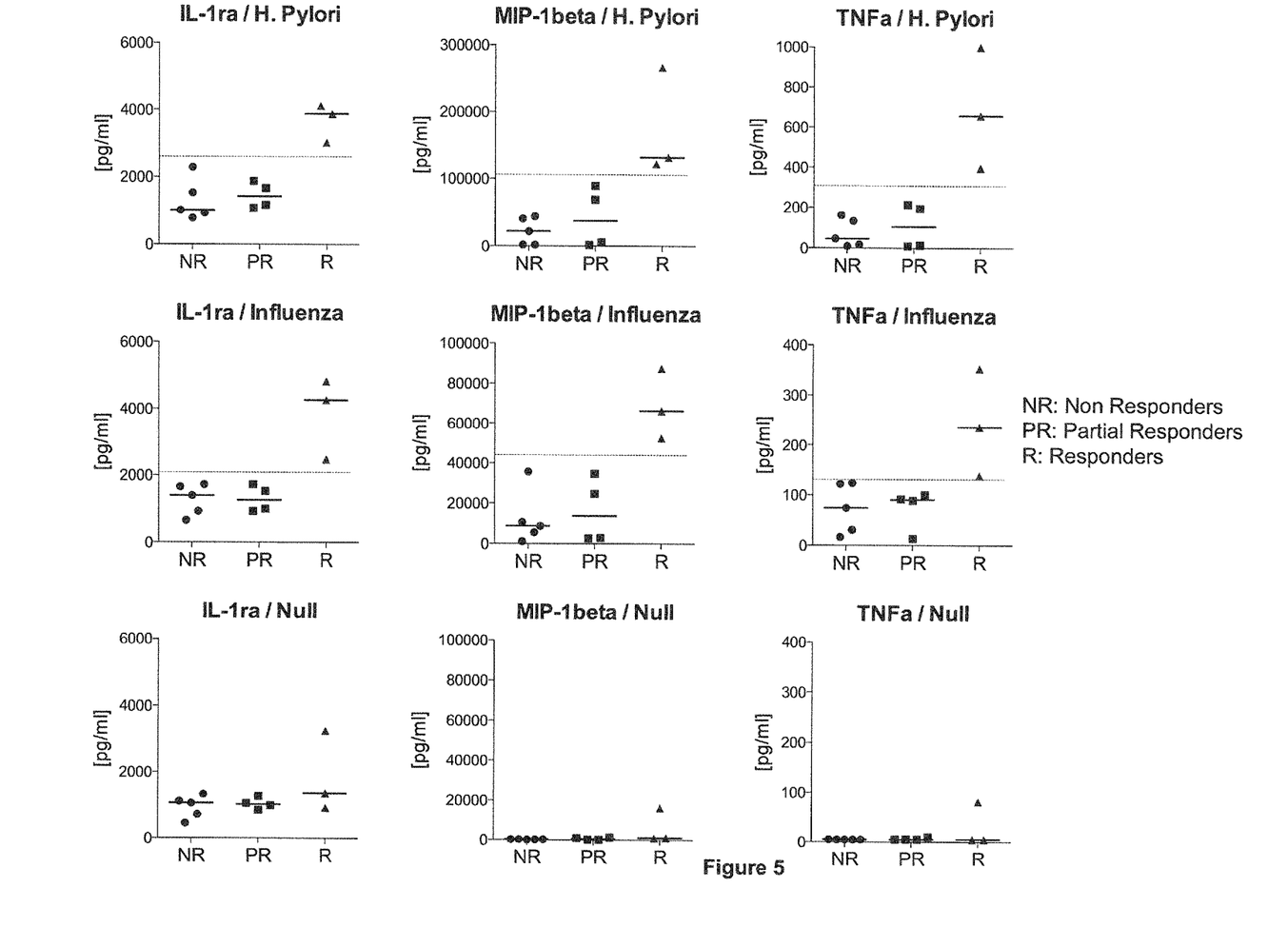
FIG. 5: Parameters correlating with therapeutic responses to TNF blockers before anti-TNF therapy. Shown are the levels of IL-1ra (left panels), MIP-1beta (middle panels) and TNF (right panels) in TruCulture supernatants following stimulation with *H. pylori* (upper panels), influenza virus (middle panels) and medium alone ("Null"; lower panels) of blood cultures from SpA patients before anti-TNF therapy (visit 1, as described for FIG. 4). Patients were grouped according to therapeutic response to TNF blockers; NR, non-responders; PR, partial responders; and R, responders. The dotted line indicates the concentration of the indicated cytokine or chemokine following stimulation that allows identification of patients responding to anti-TNF therapy.

Reference value refers to a value established by statistical analysis of values obtained from representative panels of individuals. The panels may for example depend upon the type of chronic inflammatory disease and/or TNF-blocker used in the therapy. The reference value can for example be obtained by measuring expression levels of the tested biomarker(s) in a panel of responding and a panel of non-responding patients suffering from the same type of chronic inflammatory disease as the tested patients, preferably using the same stimulating agent. A cut-off value that can discriminate responders from non-responders or responders from non-responders or partial-responders is then determined for each biomarker as shown in FIG. 5.

Differential expression refers to a higher or lower level of expression in responders compared to non-responders.

Higher or lower level refers to a significant higher or lower level, i.e., p-value inferior to 0.1.

Biologic treatment includes a wide range of products such as vaccines, blood and blood components, allergenics, somatic cells, gene therapy, tissues, and recombinant therapeutic proteins. Biologics can be composed of sugars, proteins, or nucleic acids or complex combinations of these substances, or may be living entities such as cells and tissues. Biologics are isolated from a variety of natural sources—human, animal, or microorganism—and may be produced by biotechnology methods and other cutting-edge technologies.

In some embodiments of the above method, the anti-TNF therapy is anti-TNF-alpha antibody therapy or soluble TNF-receptor based protein therapy.

In some other embodiments of the above method, said patient is a human individual. In some preferred embodiments, said patient is a newly diagnosed individual, not treated with biologic treatment after diagnosis. In some other preferred embodiments, said patient has not been treated with any TNF-blocker.

In some embodiments of the above method, the patient suffers from a chronic inflammatory disease. Preferably, a chronic inflammatory disease selected from the group comprising rheumatoid arthritis, Crohn's disease, ulcerative colitis, psoriasis, and diseases of the spondyloarthritis (SpA) group. The SpA group includes psoriatic arthritis, reactive arthritis, arthritis related to inflammatory bowel disease, and a subgroup of juvenile chronic arthritis and ankylosing spondylitis. More preferably, the chronic inflammatory disease is rheumatoid arthritis or spondyloarthritis (SpA).

The biological sample is a body fluid or biopsied cells or tissue. The biological sample is advantageously a body fluid. Preferably, the biological sample is whole-blood or peripheral blood mononuclear cells (PBMC), more preferably, whole-blood.

The culture of immune cells is prepared using methods of culturing immune cells from biological samples that are well-known in the art. The culture comprises isolated immune cells or non-isolated immune cells, and appropriate culture medium. The culture is advantageously a whole-blood cell culture or a PBMC culture, preferably a whole-blood cell culture. The immune cells are advantageously cultured in a tissue-culture container adapted to high-throughput screening such as a tube, plate, microplate and the like.

The culture is submitted to a stimulus such as a complex stimulus like a microbial stimulus, or a stimulus targeting specific signaling pathways such as innate immune responses, cytokine receptor signaling and T-cell receptor signaling.

A stimulating agent inducing a complex stimulus includes a whole-microbe, including live, attenuated or killed gram-negative bacteria, gram-positive bacteria, mycobacteria, fungi and viruses.

A stimulating agent triggering innate immune responses is advantageously a molecule of the Microbe-Associated-Molecular Pattern (MAMP), preferably a ligand of a receptor chosen from Toll-Like-Receptors (TLR) such as TLR2, TLR3, TLR4, TLR5, TLR6, TLR7, TLR8 and TLR9; Nucleotide-binding domain and Leucine-rich containing molecule (NLRs) such as NOD1 or NLRP3; C-type lectin receptors (CLRs) such as Dectin-1; Mannose receptor or collagen type I receptor (CD36). The stimulating agent is advantageously chosen from acetylated D-gamma-Glu-mDAP (CD12-iE DAP; usually in the range of 4 μg/ml), calcium pyrophosphate dehydrate (CPPD; usually in the range of 100 μg/ml), Fibroblast-Stimulating Lipopeptide-1 (FLS-1; usually in the range of 2 μg/ml), PolyI:C (usually in the range of 20 μg/ml), Lipopolysaccharide (LPS), preferably ultrapure LPS (LPS-EB; usually in the range of 10 ng/ml), Flagellin from *S. typhimurium* (Flagellin-ST; usually in the range of 0.25 μg/ml), 1-(4-Amino-2-ethylaminomethylimidazo[4,5-c]quinolin-1-yl)-2-methylpropan-2-ol; Gardiquimod™, usually in the range of 3 μg/ml), R848 (Resiquimod; usually in the range of 1 μg/ml), ODN 2216 (5'-GGGGGACGA:TCGTCGGGGGG-3' (SEQ ID NO: 1); in the range of 25 μg/ml), liporabinomannan (in the range of 10 μg/ml), Yeast-derived particulate β-glucan (WGP; usually in the range of 40 μg/ml) and Zymosan (usually in the range of 1-10 μg/ml).

A stimulating agent triggering cytokine receptor signaling is advantageously a cytokine, preferably a cytokine chosen from Interferon-alpha, in particular Interferon-alpha 2b (in the range of 1,000 IU/ml); Interferon-beta (usually in the range of 1,000 IU/ml); Interferon-gamma (in the range of 1,000 IU/ml); TNF-alpha (usually in the range of 10 ng/ml); IL-1 beta (usually in the range of 25 ng/ml) and IL-23 (usually in the range of 50 ng/ml).

A stimulating agent triggering T-cell receptor signaling is preferably a T-cell receptor cross linking agent such as for example a mixture of anti-CD3 antibody (usually in the range of 0.4 μg/ml) and anti-CD28 antibody (usually in the range of 0.33 μg/ml) or a superantigen such as for example Staphylococcal enterotoxin B (Enterotoxin SEB; usually in the range of 0.4 μg/ml).

The stimulation of the culture of immune cells is performed for a time sufficient to induce an immune response in the culture; usually the stimulation is from about 4 to 24 hours.

In some embodiment of the method, the stimulating agent is chosen from a heat-killed live, attenuated or killed microbe and a Toll-like receptor agonist. Preferably, the stimulating agent is chosen from heat-killed gram-negative bacteria, in particular *Helicobacter pylori*; heat-killed gram-positive bacteria, in particular, *Staphylococcus aureus*; heat-killed yeast, in particular, *Candida albicans*, and live viruses, in particular Influenza A virus. In some more preferred embodiments, the stimulating agent is chosen from heat-killed *Helicobacter pylori* and live Influenza A virus.

The biomarker according to the invention is a predictive biomarker; it is defined as a gene that is:
(i) induced in immune cells in response to an innate or adaptive immune response stimulus, and
(ii) expressed at a higher or lower level (mRNA and/or protein level) in stimulated immune cells between responder and non-responder patients.

The biomarker can be determined using a method of determining a predictive biomarker of response to anti-TNF therapy, comprising the steps of:
(i) obtaining a group of patients with clinical indications for anti-TNF treatment, and for each patient of the group:
(ii) preparing a culture of immune cells from a biological sample collected from the patient before initiation of anti-TNF treatment,
(iii) stimulating the culture with an agent that stimulates the innate or adaptive immune system, and
(iv) measuring the expression level (mRNA or protein) of different genes that are induced in response to an innate or adaptive immune response stimulus;
(v) administering the anti-TNF treatment to the patients and after a time sufficient to induce a clinical response, classifying patients in a responder group and a in a non-responder group based on clinical assessment, and (vi) determining the genes that are differentially expressed in the responder-group compared to the non-responder group, corresponding to predictive biomarker(s) of response to anti-TNF therapy.

Responder and non-responder groups are determined using objective criteria for evaluating the response to anti-TNF treatment, such as clinical scores that are well-known in the art. For example, clinical assessment may be performed three months after therapy initiation.

The analyzed genes include genes induced by innate or adaptive immune responses stimuli, in particular genes induced by MAMP such as genes induced by Toll-Like-Receptors, NLRs, C-type lectin receptors and CD36 signaling; genes induced by cytokine receptor signaling, and genes induced by T-cell receptor signaling, which are well-known in the art. The analyzed genes are advantageously cytokine genes expressed by monocytes or genes coding for inflammatory cytokines such as genes coding for inflammatory chemokines.

In some embodiments, the method of determining a predictive biomarker comprises determining a combination of genes that are differentially expressed to determine a signature of response to anti-TNF therapy.

Gene expression including biomarker gene expression may be measured at the protein or mRNA level. Protein expression may be assayed directly on the cell culture supernatant. RNA expression is assayed after lysing cells, extracting and precipitating RNA according to well-known methods.

Measurement of protein levels may be achieved using several different techniques, many of which are antibody-based. Example of such techniques include with no limitations immunoassays (Enzyme-linked immunoassay (ELISA), radioimmunoassay, chemiluminescence- and fluorescence-immunoassay), immunohistochemistry assays and antibody microarray-based assays. Preferably, protein level is measured using an immunoassay such as ELISA. Antibodies specific for cytokines and metalloproteinases are well-known in the art and various sensitive immunoassays, in particular multiplex assays for measuring several biomarkers simultaneously are available.

mRNA levels may be measured, either by hybridization to a specific probe, eventually labeled with a detectable label and/or immobilized on the surface of a solid support (plate, slide, strip, wells, microparticles, fiber, gel), or by amplification using specific primers, eventually labeled with a detectable label. Preferably, the mRNA level is measured by quantitative reverse transcription polymerase chain reaction (qRT-PCR) assay or direct mRNA counting technology (nCounter).

The biomarker encompasses any gene that is differentially expressed in responders compared to non-responders in response to an innate or adaptive immune responses stimulus as defined above.

The biomarker is advantageously a human biomarker.

In some embodiments, the biomarker is a cytokine or a matrix metalloproteinase (MMP). Cytokines include Chemokine, Interferon (IFN), Interleukin (IL-), TNF family, CSF (colony Stimulating factor) and TGF (Transforming Growth Factor) molecules. In particular, cytokines include: Interleukin-1 beta (IL-1 beta), Interleukin-2 (IL-2), Interleukin-4 (IL-4), Interleukin-6 (IL-6), Interleukin-10 (IL-10), Interleukin-17 (IL-17), Interleukin-12p70 (IL-12p70), Interleukin-1 receptor antagonist (IL-1ra), Macrophage Inflammatory Protein-1 beta (MIP-1 beta), Macrophage Inflammatory Protein-1 alpha (MIP-1 alpha), Tumor Necrosis factor-alpha (TNF-alpha), Tumor Necrosis factor-beta (TNF-beta), Interferon-gamma (IFN-gamma), Chemokine ligand 2 (CCL2), also called Monocyte Chemoattractant Protein 1 (MCP1), Brain-Derived Neurotrophic Factor (BDNF) and Eotaxin-1. Metalloproteinases include in particular MMP-9.

In some more preferred embodiments, the cytokine is an inflammatory cytokine. Inflammatory cytokines include in particular IL-1 alpha, IL-1 beta, IL-6, TNF-alpha, INF-gamma, chemokines, IL-12, IL-17, IL-18, IL-20 and IL-23 LIF; more particularly IL-1 alpha, IL-1 beta, IL-6 and TNF-alpha.

In other preferred embodiments, the cytokine is a cytokine secreted by monocytes. Cytokines secreted by monocytes include in particular IL-1 alpha, IL-1 beta, IL-1ra, TNF-alpha.

Preferably, the biomarker is selected from the group consisting of: IFN-gamma, IL-1 beta, IL-12p70, IL-1ra, IL-17, IL-2, IL-4, MCP1, MIP-1 alpha, MIP-1 beta, MMP-9, TNF-alpha and TNF-beta, more preferably IL-1ra, MIP-1 beta, MMP-9, and TNF-alpha; even more preferably IL-1ra MIP-1 beta and MMP-9.

Biomarker sequences (polypeptidic and nucleotidic) are well-known in the art and available in public data bases, as shown here:

TABLE 1

| Human sequences | |
| --- | --- |
| Gene name | Protein Accession number |
| IFN-gamma | SwissProt P01579 |
| IL-1 beta | SwissProt P01584 |
| IL-12p70 | SwissProt P29459 |
| IL-17 | SwissProt Q16552 |
| IL-1ra | SwissProt P18510 |
| IL-2 | SwissProt P60568 |
| IL-4 | SwissProt P05112 |
| MCP1 | SwissProt P13500 |
| MIP-1 alpha | SwissProt P10147 |
| MIP-1 beta | SwissProt P13236 |
| MMP-9 | SwissProt P14780 |
| TNF-alpha | SwissProt P01375 |
| TNF-beta | SwissProt P01374 |

In some embodiments, the above prediction method comprises a step of determining a predictive biomarker of response to anti-TNF therapy prior to step a). The biomarker can be determined by the above described method of determination of a predictive biomarker of response to anti-TNF therapy.

The prediction method of the invention can be performed simultaneously or subsequently on several patients (high-throughput method).

In some embodiments, the above prediction method comprises a further step of sorting the patient(s) into responder(s) or non responder(s) based on biomarker expression level(s) after immune stimulation.

In some other embodiments, the method of the invention is performed simultaneously on several different biomarkers, in particular on a protein or mRNA signature of response to anti-TNF therapy as defined above.

A preferred method according to the invention is a method for predicting the therapeutic response to anti-TNF therapy in a patient of the SpA group, comprising measuring the expression level of at least one biomarker selected from the group consisting of: IL-1ra, MIP-1 beta, MMP-9, and TNF-alpha; preferably IL-1ra MIP-1 beta and MMP-9. The biomarker is advantageously measured after stimulation of the immune cells with heat-killed *Helicobacter pylori* or live Influenza A virus. In addition, the protein level of the biomarker is advantageously measured. A higher level of the protein biomarker compared to the reference value determined in a group of non-responder patients indicates that the patient will respond to anti-TNF therapy.

The invention relates also to the use of a gene that is induced in immune cells in response to an innate or adaptive immune response stimulus, and is expressed at a higher or lower level (mRNA and/or protein level) in stimulated immune cells between responder and non-responder patients as a predictive biomarker to therapeutic response to anti-TNF therapy. The invention encompasses the use of any gene/biomarker as mentioned above, in particular a gene obtainable or obtained by the above described method of determining a predictive biomarker of response to anti-TNF therapy.

The invention relates also to the above described method of determining a predictive biomarker of response to anti-TNF therapy.

The invention relates also to a method of treating a patient with a TNF-blocker, comprising the steps of:
 determining if the patient will respond to anti-TNF therapy by performing the method of prediction of response to anti-TNF therapy according to the invention, and
 administering the TNF-blocker to the patient by any means, if the patient has been determined as responder.

The invention relates also to a TNF-blocker for use in the therapy of a chronic inflammatory disease in a patient, wherein the TNF-blocker is administered to a patient that has been classified as responder by performing the method of predicting a therapeutic response to anti-TNF therapy according to the invention.

The invention relates also to a TNF-blocker and another anti-inflammatory drug for use in the therapy of a chronic inflammatory disease in a patient, wherein the TNF-blocker is administered to a patient, which has been classified as responder by performing the method of predicting a therapeutic response to anti-TNF therapy according to the invention, and the other anti-inflammatory agent is administered to a patient that has been classified as non-responder by performing the method of predicting a therapeutic response to anti-TNF therapy according to the invention.

The practice of the present invention will employ, unless otherwise indicated, conventional techniques, which are within the skill of the art. Such techniques are explained fully in the literature.

In addition to the preceding features, the invention further comprises other features that will emerge from the description that follows, which refers to examples illustrating the methods and uses according to the present invention, as well as to the appended drawings in which:

FIG. 4: Immunologic parameters before anti-TNF therapy that correlate with subsequent therapeutic responses to TNF-blockers. Patients were grouped into non-responders (white squares), partial responders (grey squares), and responders (black squares) based on the improvement score as described in FIG. 3. Samples collected before initiation of anti-TNF therapy (Visit 1) were stimulated with 20 different immune stimuli, and 32 secreted molecules were analyzed for each assay. A multi-group comparison of the 640 parameters was performed to identify combinations of analytes and stimuli (rows) that can discriminate the three patient groups before initiation of anti-TNF therapy. Hierarchical clustering shows that patients responding to anti-TNF therapy (high improvement score) express higher levels (indicated by the light shading in the heat map) of IL-1ra, MIP-1beta and other secreted molecules in response to specific stimuli, compare to non-responders or partial responders.

EXAMPLE: IMMUNOLOGIC PARAMETERS PREDICTING THERAPEUTIC RESPONSES TO TNF BLOCKERS IN SpA PATIENTS

Developing biomarkers that will help patients and physicians to choose the most effective therapy is an unmet medical need that needs to be urgently addressed. To address this issue, the inventors have hypothesized that the analysis of the immune functions of patients will allow them to define objective criteria (biomarkers) to predict therapeutic responses to anti-TNF therapy. This hypothesis was tested in a pilot study involving 12 SpA patients with axial involvement and indications for anti-TNF treatment, using the "TruCulture" system disclosed in Duffy et al. (2014) for analyzing the immune response of the patients.

Figure 1:
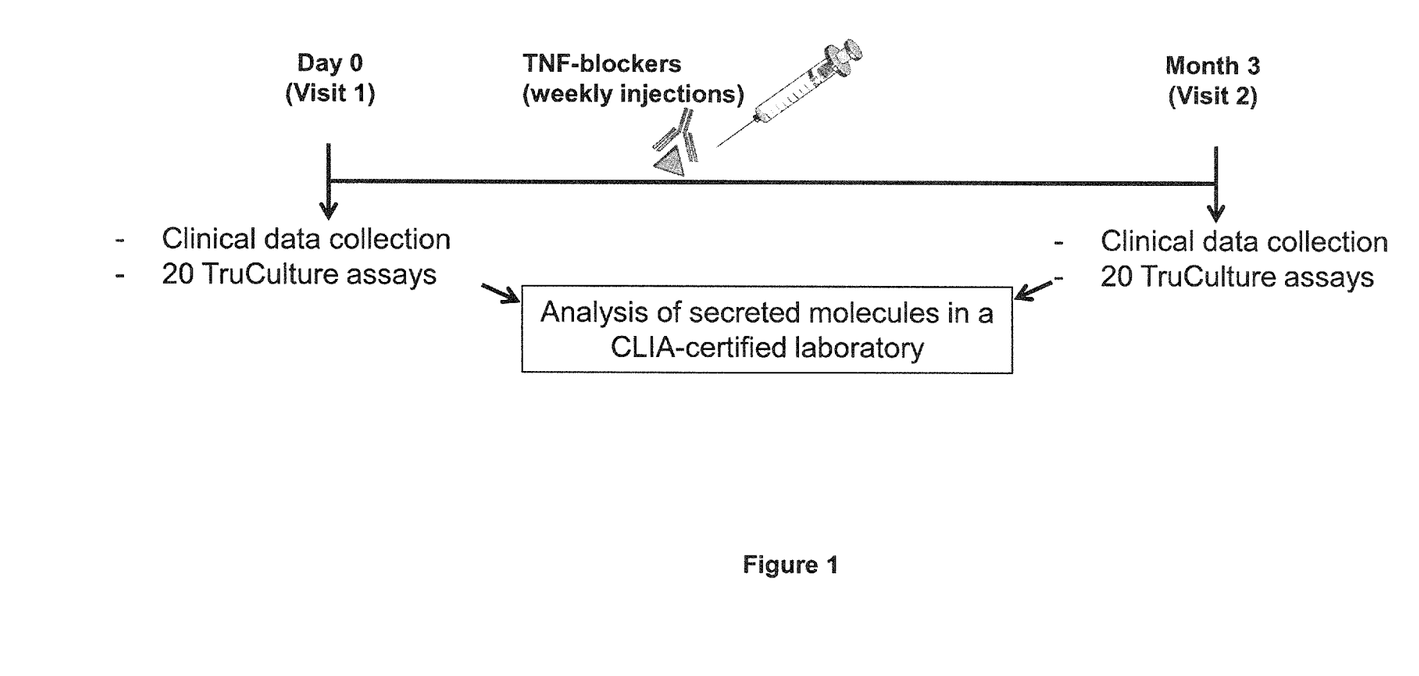
FIG. 1: Design of the pilot study. Twelve patients with a definitive diagnosis of SpA and indications for treatment with TNF-blockers were enrolled. Blood samples were collected prior to starting treatment with TNF blockers, and 3 months after the beginning of anti-TNF therapy. Clinical and biological efficacy was monitored at week 12 according to the current standard of care.

The study was designed to address two questions; (i) what is the impact of anti-TNF therapy on immune responses to microbial challenges and stimuli targeting specific pathways in SpA patients? and (ii) is it possible to identify immunological correlates of responsiveness to TNF blockers before the initiation of anti-TNF therapy? The design of the study is shown in FIG. 1.

1. Patients and Methods

Patients

Peripheral blood samples were obtained from 12 patients with spondyloarthritis in the Department of Rheumatology (Cochin Hospital, Paris, France). All the patients met either the modified New York criteria for ankylosing spondylitis or the Amor criteria for spondyloarthritis (Amor et al., 1990; van der Linden et al., 1984). Age, sex, disease duration, HLA-B27 positivity and the type of clinical presentation (axial involvement, peripheral arthritis, enthesis and non rheumatologic symptoms) were recorded. Current treatment was also noted at the time of sampling. The patients were all adults and had never received biologic anti-rheumatic agents. The first sample (visit 1) was obtained before anti-TNF therapy and the second sample three months after initiation of anti-TNF therapy. Sampling for visit 2 was performed one week after the last injection of TNF blockers (Etanercept for 11 patients and Adalimumab for 1 patient).

The study was approved by the Ethical Review Committee "Comité de Protection des Personnes Ile de France III" and written informed consent was given by all patients prior to inclusion in the study.

Whole Blood Assays to Assess Immune Responses in SpA Patients

Whole blood assays was performed using the same standardized and validated procedure as previously disclosed in Duffy et al., 2014. Briefly, TruCulture tubes were prepared in batch with the indicated stimulus, resuspended in a volume of 2 ml buffered media and maintained at −20° C. until time of use. Blood was obtained from the antecubital vein using vacutainers coated with Sodium-Heparin. Within twenty minutes of collection, 1 ml of whole blood was distributed into each of the pre-warmed TruCulture tubes, inserted into a dry block incubator and maintained at 37° C., room air for 22 hr. At the end of the incubation period, tubes were opened and a valve was inserted in order to separate the sedimented cells from the supernatant and to stop the stimulation reaction. Liquid supernatants were aliquoted and immediately frozen at −80° C. until the time of use. 32 secreted molecules were analyzed in a CLIA-certified laboratory using Human CytokineMAP® A and B (Myriad RBM).

Statistical Analysis

A two-tailed Wilcoxon matched-pairs test was used to analyze the effects of anti-TNF therapy on the production of cytokines and chemokines. Agglomerative hierarchical clustering, paired t-test (FIG. 2) and ANOVA testing (FIG. 4) were performed with Qlucore Omics Explorer, version 3.0 (Qlucore, Lund, Sweden).

2. Results

TNF Blockers Affect Immune Responses in SpA Patients

Freshly drawn whole blood was stimulated in TruCulture tubes with 20 different stimuli for 22 hours as described above. Supernatants were frozen at −80° C. and 32 secreted molecules were analyzed in a CLIA-certified laboratory. First, the levels of secreted molecules in the supernatants of TruCulture assays were compared before and 3 months after initiation of anti-TNF therapy. A highly significant reduction of the secretion of IL-1ra in response to microbial stimuli such as gram-positive bacteria (*S. aureus*), gram-negative bacteria (*H. pylori*), yeast (*C. albicans*) and viruses (influenza) was noted in blood samples collected 3 months after start of anti-TNF therapy. Production of IL-1ra was also strongly reduced following stimulation with agonists targeting specific toll-like receptors (TLRs), such as LPS, and gardiquimod. Reduced production of other pro-inflammatory cytokines and chemokines, such as IL-6 and MIP-1β, were also observed in blood samples from patients after treatment with TNF blockers.

Figure 2:
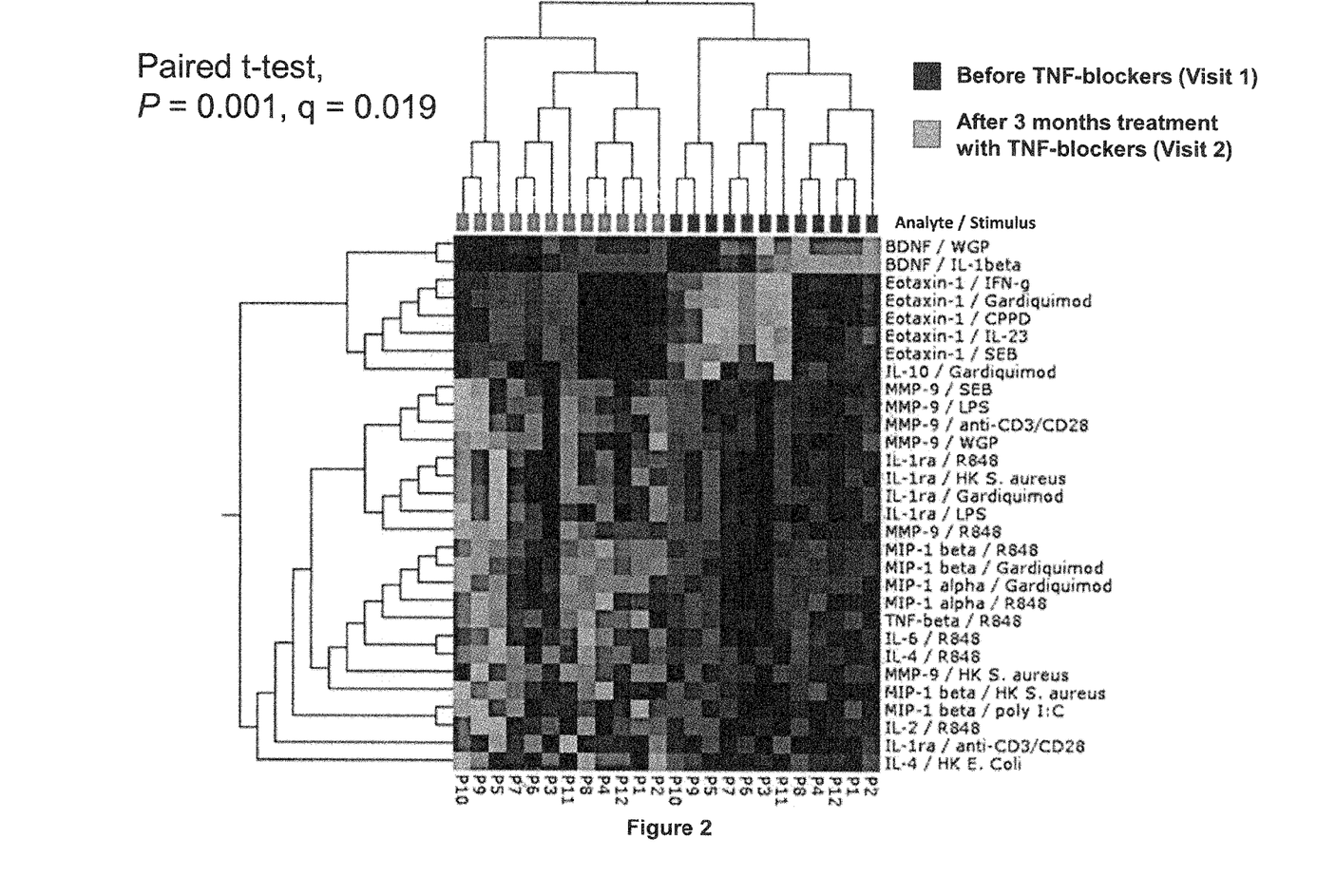
FIG. 2: An Immunologic signature of anti-TNF therapy. The levels of 31 secreted molecules (analytes) in response to 18 immune stimuli included in each of the TruCulture assays were compared in samples from patients obtained before (visit 1, black rectangles) and 3 months after initiation of anti-TNF therapy (visit 2, grey rectangles). The stimuli TNF and TNF+IL-1β, as well as TNF levels in the supernatant were excluded from the analysis because of possible interference with residual TNF blockers in the circulation of SpA patients. Shown is a heat map representation generated by agglomerative hierarchical clustering using Qlucore Omics explorer software (version 3.0). Of the 558 combinations tested, 30 reached a significance level of at least 0.001 (Wilcoxon matched-pairs test).

To obtain an overview of the effects of anti-TNF therapy on immune responses in SpA patients, a comprehensive analysis was performed by comparing the levels of 31 secreted molecules in response to 18 immune stimuli included in each of the TruCulture assays. The stimuli TNF and TNF+IL-1, as well as TNF levels in the supernatant were excluded from the analysis because of possible interference with residual TNF blockers in the circulation of SpA patients. FIG. 2 shows a heat map representation of a paired analysis of the levels of 31 secreted molecules induced by 18 stimuli. Of the 558 combinations tested, 30 reached a significance level of at least 0.001 (Wilcoxon matched pairs test). This analysis revealed that in addition to several pro-inflammatory cytokines and chemokines, the levels of the matrix metalloproteinase MMP-9 were significantly reduced in response to several stimuli after anti-TNF therapy. Also, the levels of the chemokine eotaxin-1 (CCL11) and of brain-derived neurotrophic factor (BDNF) were increased in blood samples from patients obtained after treatment with TNF blockers.

Together, these data show that anti-TNF therapy strongly affects the immune responses of patients to various pathogens as well as to stimuli targeting specific signaling pathways. It is also important to note that the effects of anti-TNF therapy on immune responses can be measured when immune cells are challenged, but not at steady state ("null stimulus" cultures).

Figure 4:
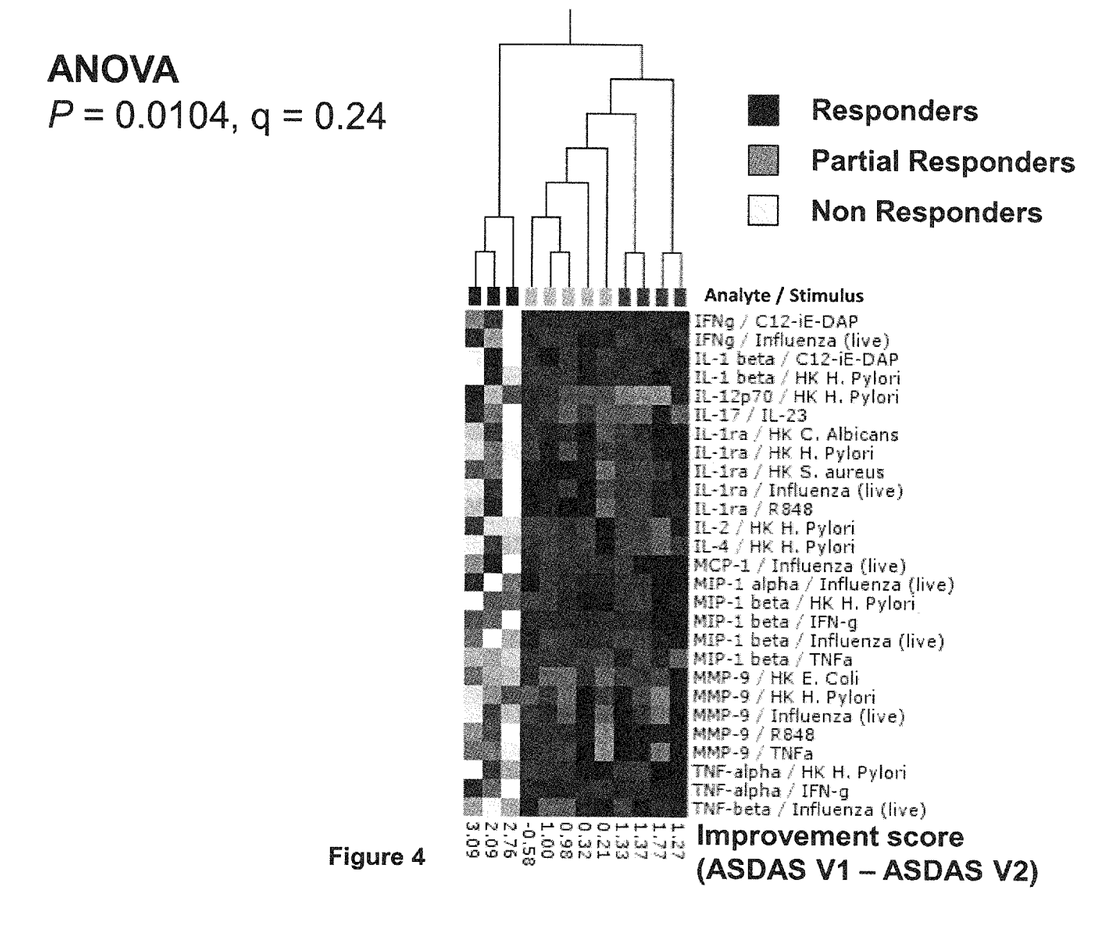

Immunologic Parameters Predicting Therapeutic Responses to TNF Blockers in SpA Patients Given the robust effects of anti-TNF therapy on immune responses to microbial challenges and agonists triggering various signaling pathways in SpA patients, the inventors next asked whether they could establish a correlation between the responses of immune cells to specific stimuli and the therapeutic response to TNF-blockers. For this, the "Ankylosing Spondylitis Disease Activity Score" (ASDAS) (Machado et al., 2011; Machado et al., 2015; van der Heijde et al., 2009) was calculated before treatment and 3 months after initiation of anti-TNF therapy and the "Improvement Score" ($ASDAS_{before\ treatment} - ASDAS_{after\ treatment}$) was determined. Patients were grouped into three groups according to the improvement score. Among the 12 patients recruited to the pilot study, 3 (25%) showed a major improvement (responders), 4 (33%) had a clinically important improvement (partial responders), and 5 (42%) did not respond to anti-TNF therapy (FIG. 3). Then a multi-group comparison (ANOVA) was performed to identify immune parameters that correlate with therapeutic responses to TNF blockers. The data show that SpA patients who secreted the highest levels of inflammatory molecules in response to immune stimuli before initiation of anti-TNF therapy have the best therapeutic responses (highest improvement score) (FIG. 4). Among the 20 stimuli and 32 cytokines and chemokines tested in this analysis, the levels of IL-1ra, MIP-1 and TNF following stimulation with *H. Pylori* and influenza virus were substantially higher in SpA patients with a major improvement after anti-TNF therapy than patients with a partial therapeutic response or non-responding patients (FIG. 5). In fact, cut-off values for the concentrations of each of these molecules in response to the two stimuli that can discriminate patients responding to anti-TNF therapy from those not-responding or only with a partial response have been identified. In contrast, the low levels of these molecules in TruCulture assays not containing stimuli did not allow prediction of therapeutic responses (FIG. 5, lower panels).

These results demonstrate that the analysis of immune responses to specific stimuli in patients before therapy is an efficient strategy to develop biomarkers to predict therapeutic efficacy of TNF-blockers.

CONCLUSIONS

1) Anti-TNF therapy alters immune responses to pathogens and stimuli targeting specific pathways in SpA patients.
2) These changes can be detected in stimulated immune cells, but not at baseline.
3) The inventors have identified combinations of stimuli and cytokines and chemokines that correlate with therapeutic response to TNF-blockers.
4) Analyzing immune responses to specific stimuli in patients before therapy is a novel and efficient strategy to develop biomarkers predicting therapeutic responses to TNF-blockers.

REFERENCES

Amor, B., Dougados, M., and Mijiyawa, M. (1990). Criteria of the classification of spondylarthropathies. Revue du rhumatisme et des maladies osteo-articulaires 57, 85-89.

Baeten, D., Baraliakos, X., Braun, J., Sieper, J., Emery, P., van der Heijde, D., McInnes, I., van Laar, J. M., Landewe, R., Wordsworth, P., et al. (2013a). Anti-interleukin-17A monoclonal antibody secukinumab in treatment of ankylosing spondylitis: a randomised, double-blind, placebo-controlled trial. Lancet 382, 1705-1713.

Baeten, D., Breban, M., Lories, R., Schett, G., and Sieper, J. (2013b). Are spondylarthritides related but distinct conditions or a single disease with a heterogeneous phenotype? Arthritis Rheum 65, 12-20.

Braun, J., Listing, J., and Sieper, J. (2005). Reply. Arthritis & Rheumatism 52, 4049-4050.

Dougados, M., and Baeten, D. (2011). Spondyloarthritis. Lancet 377, 2127-2137.

Duffy, D., Rouilly, V., Libri, V., Hasan, M., Beitz, B., David, M., Urrutia, A., Bisiaux, A., Labrie, S. T., Dubois, A., et al. (2014). Functional Analysis via Standardized Whole-Blood Stimulation Systems Defines the Boundaries of a Healthy Immune Response to Complex Stimuli. Immunity 40, 436-450.

International Genetics of Ankylosing Spondylitis, C., Cortes, A., Hadler, J., Pointon, J. P., Robinson, P. C., Karaderi, T., Leo, P., Cremin, K., Pryce, K., Harris, J., et al. (2013). Identification of multiple risk variants for ankylosing spondylitis through high-density genotyping of immune-related loci. Nature genetics 45, 730-738.

Jenkinson, T. R., Mallorie, P. A., Whitelock, H. C., Kennedy, L. G., Garrett, S. L., and Calin, A. (1994). Defining spinal mobility in ankylosing spondylitis (AS). The Bath AS Metrology Index. J Rheumatol 21, 1694-1698.

Machado, P., Landewe, R., Lie, E., Kvien, T. K., Braun, J., Baker, D., van der Heijde, D., and Assessment of SpondyloArthritis international, S. (2011). Ankylosing Spondylitis Disease Activity Score (ASDAS): defining cut-off values for disease activity states and improvement scores. Ann Rheum Dis 70, 47-53.

Machado, P., Navarro-Compan, V., Landewe, R., van Gaalen, F. A., Roux, C., and van der Heijde, D. (2015). Calculating the ankylosing spondylitis disease activity score if the conventional c-reactive protein level is below the limit of detection or if high-sensitivity c-reactive protein is used: an analysis in the DESIR cohort. Arthritis & rheumatology 67, 408-413.

Robinson, P. C., and Brown, M. A. (2014). Genetics of ankylosing spondylitis. Molecular immunology 57, 2-11.

Rudwaleit, M., Jurik, A. G., Hermann, K. G., Landewe, R., van der Heijde, D., Baraliakos, X., Marzo-Ortega, H., Ostergaard, M., Braun, J., and Sieper, J. (2009). Defining active sacroiliitis on magnetic resonance imaging (MRI) for classification of axial spondyloarthritis: a consensual approach by the ASAS/OMERACT MRI group. Ann Rheum Dis 68, 1520-1527.

Rudwaleit, M., Metter, A., Listing, J., Sieper, J., and Braun, J. (2006). Inflammatory back pain in ankylosing spondylitis: a reassessment of the clinical history for application as classification and diagnostic criteria. Arthritis Rheum 54, 569-578.

Smith, J. A., and Colbert, R. A. (2014). Review: The interleukin-23/interleukin-17 axis in spondyloarthritis pathogenesis: Th17 and beyond. Arthritis & rheumatology 66, 231-241.

Thomas, S., Rouilly, V., Patin, E., Alanio, C., Dubois, A., Delval, C., Marquier, L. G., Fauchoux, N., Sayegrih, S., Vray, M., et al. (2015). The Milieu Interieur study—an integrative approach for study of human immunological variance. Clinical immunology 157, 277-293.

van der Heijde, D., Lie, E., Kvien, T. K., Sieper, J., Van den Bosch, F., Listing, J., Braun, J., and Landewe, R. (2009). ASDAS, a highly discriminatory ASAS-endorsed disease activity score in patients with ankylosing spondylitis. Ann Rheum Dis 68, 1811-1818.

van der Linden, S., Valkenburg, H. A., and Cats, A. (1984). Evaluation of diagnostic criteria for ankylosing spondylitis. A proposal for modification of the New York criteria. Arthritis Rheum 27, 361-368.

The invention claimed is:

1. A method, comprising:
   a) obtaining a culture of immune cells from a biological sample taken from a patient having a chronic inflammatory disease, wherein the biological sample is collected prior to an anti-TNF therapy;
   b) stimulating the culture of immune cells with an agent that stimulates the innate or adaptive immune system; and
   c) measuring the expression level in the culture of immune cells of at least one cytokine and/or matrix metalloproteinase (MMP).

2. The method according to claim 1, wherein said chronic inflammatory disease is rheumatoid arthritis or a disease of the spondyloarthritis (SpA) group.

3. The method of claim 2, wherein the SpA group disease is selected from psoriatic arthritis, reactive arthritis, arthritis related to inflammatory bowel disease, a subgroup of juvenile chronic arthritis and ankylosing spondylitis.

4. The method according to claim 1, wherein said agent that stimulates the innate or adaptive immune system is chosen from a heat-killed live, attenuated or killed microbe and a Toll-like receptor agonist.

5. The method of claim 1, wherein the culture of immune cells is stimulated with *Helicobacter pylori* or Influenza A virus.

6. The method of claim 1, wherein the cytokine is selected from the group consisting of: IFN-gamma, IL-1 beta, IL-12p70, IL-1ra, IL-17, IL-2, IL-4, MCP1, MIP-1 alpha, MIP-1 beta, TNF-alpha and TNF-beta and the MMP is MMP-9.

7. The method of claim 1, wherein the expression level is measured by measuring mRNA expression level.

8. The method of claim 1, wherein the expression level is measured by measuring protein expression level.

9. The method of claim 6, wherein the expression level of the at least one of IL-1ra, MIP-1beta, and TNF-alpha is increased.

10. The method of claim 6, wherein the expression level of IL-1ra is increased, the expression level of MIP-1beta is increased, and the expression level of TNF-alpha is increased.

11. The method of claim 1, wherein the biological sample taken from a patient is whole blood.

12. A method, comprising:
    a) obtaining a first culture of immune cells from a biological sample taken from a patient having a chronic inflammatory disease, wherein the biological sample is collected prior to an anti-TNF therapy;
    b) stimulating the first culture of immune cells with a first agent that stimulates the innate or adaptive immune system;
    c) measuring the expression level in the first culture of immune cells of at least one cytokine and/or matrix metalloproteinase (MMP) in the first culture of immune cells;
    d) obtaining a second culture of immune cells from the patient;
    e) stimulating the second culture of immune cells with a second agent that stimulates the innate or adaptive immune system; and
    f) measuring the expression level in the second culture of immune cells of at least one cytokine and/or matrix metalloproteinase (MMP) in the second culture.

13. The method according to claim 12, wherein said chronic inflammatory disease is rheumatoid arthritis or a disease of the spondyloarthritis (SpA) group.

14. The method of claim 13, wherein the SpA group disease is selected from psoriatic arthritis, reactive arthritis, arthritis related to inflammatory bowel disease, a subgroup of juvenile chronic arthritis and ankylosing spondylitis.

15. The method of claim 14, wherein the SpA group disease is ankylosing spondylitis.

16. The method of claim 12, wherein the expression level of IL-1ra, MIP-1beta, and TNF-alpha is measured in the first culture of immune cells and the expression level of IL-1ra, MIP-1beta, and TNF-alpha is measured in the second culture of immune cells.

17. The method of claim 12, wherein the expression level is measured by measuring mRNA expression level.

18. The method of claim 12, wherein the expression level is measured by measuring protein expression level.

19. The method of claim 12, wherein the expression level of the at least one of IL-1ra, MIP-1beta, and TNF-alpha is increased in the first culture of immune cells and in the second culture of immune cells.

20. The method of claim 12, wherein the expression level of IL-1ra is increased, the expression level of MIP-1beta is increased, and the expression level of TNF-alpha is increased in the first culture of immune cells; and wherein the expression level of IL-1ra is increased, the expression level of MIP-1beta is increased, and the expression level of TNF-alpha is increased in the second culture of immune cells.

21. A method, comprising:
    a) obtaining a culture of immune cells from a biological sample taken from a patient having a chronic inflammatory disease, wherein the biological sample is collected prior to an anti-TNF therapy;
    b) stimulating the culture of immune cells with an agent that stimulates the innate or adaptive immune system; and
    c) measuring the expression level in the culture of immune cells of IL-1ra, MIP-1beta, and TNF-alpha;
    wherein the expression level of IL-1ra is increased, the expression level of MIP-1beta is increased, and the expression level of TNF-alpha is increased.

22. A method, comprising:
    a) obtaining a first culture of immune cells from a biological sample taken from a patient having a chronic inflammatory disease, wherein the biological sample is collected prior to an anti-TNF therapy;
    b) stimulating the first culture of immune cells with a first agent that stimulates the innate or adaptive immune system;
    c) measuring the expression level in the first culture of immune cells of IL-1ra, MIP-1beta, and TNF-alpha;
    d) obtaining a second culture of immune cells from the patient;
    e) stimulating the second culture of immune cells with a second agent that stimulates the innate or adaptive immune system; and
    f) measuring the expression level in the second culture of immune cells of IL-1ra, MIP-1beta, and TNF-alpha;
    wherein the expression level of IL-1ra is increased, the expression level of MIP-1beta is increased, and the expression level of TNF-alpha is increased in the first culture of immune cells; and
    wherein the expression level of IL-1ra is increased, the expression level of MIP-1beta is increased, and the expression level of TNF-alpha is increased in the second culture of immune cells.

* * * * *